United States Patent [19]

Brandon et al.

[11] Patent Number: 4,959,310
[45] Date of Patent: Sep. 25, 1990

[54] MONOCLONAL ANTIBODIES TO SOYBEAN KUNITZ TRYPSIN INHIBITOR AND IMMUNOASSAY METHODS

[75] Inventors: David L. Brandon, Berkeley; Anne H. Bates, LaFayette; Mendel Friedman, Moraga, all of Calif.

[73] Assignee: The United States of America as represented by the Secretary of Agriculture, Washington, D.C.

[21] Appl. No.: 101,918

[22] Filed: Sep. 28, 1987

[51] Int. Cl.$^5$ .................. C12P 21/08; C12N 5/18; G01N 33/577; A61K 39/395
[52] U.S. Cl. ..................... 435/7; 435/172.2; 435/240.27; 435/23; 436/548; 530/387
[58] Field of Search .......... 435/7, 184, 172.2, 240.27, 435/23; 530/387; 436/548, 533, 86, 808, 809; 426/231

[56] References Cited

U.S. PATENT DOCUMENTS 4,196,265 4/1980 Koprowski et al. ............... 424/85 X
4,271,145 6/1981 Wands .................................. 435/948

OTHER PUBLICATIONS

Oellerich, M., J. Clin. Chem. Clin. Biochem., vol. 22 (1984) pp. 895-904 "Enzyme-Immunoassay: A Review".
Sevier, E. D., Clin. Chem. 27/11 (1981) pp. 1797-1806 "Monoclonal Antibodies in Clinical Immunology".
D. L. Brandon, S. Hague, and M. Friedman, "Antigenicity of Native and Modified Kunitz Soybean Trypsin Inhibitor" (Abstract), 7th European Immunology Meeting, Jerusalem, Israel, Sep. 8-13 (1985).
D. L. Brandon and M. Friedman, "Food Processing to Reduce Protein Allerginicity" (Abstract), 6th International Congress of Immunology, Toronto, Canada, Jul. 6-11 (1986).
N. Catsimpoolas and E. Leuthner, "Immunological Methods for Detection and Quantitation of Kunitz Soybean Trypsin Inhibitor," *Analytical Biochemistry* 31: 437-447 (1969).
N. Catsimpoolas, D. A. Rogers, and E. W. Meyer, "Immunochemical and Disc Electrophoresis Study of Soy- (List continued on next page.)

*Primary Examiner*—Esther M. Kepplinger
*Assistant Examiner*—Laurie A. Scheiner
*Attorney, Agent, or Firm*—M. Howard Silverstein; John D. Fado; Margaret A. Connor

[57] ABSTRACT

Hybrid cell lines (hybridomas) which produce and secrete monoclonal antibodies with three distinct patterns of recognition are described. The first specificity pattern is defined by antibodies which (1) recognize Kunitz trypsin inhibitor (KTI), one of the principal protease inhibitors found in soybeans, but do not detect the Bowman-Birk inhibitors (BBI), the other major class of protease inhibitors in soybeans; (2) bind to native KTI isoforms a and b but do not react with KTI isoforms a and b which have been denatured by moist heat or alkaline treatment or which have been subjected to disulfide exchange; and (3) do not recognize native KTI isoform c. The second specificity pattern is defined by antibodies that (1) recognize KTI, but do not bind BBI; (2) bind native KTI isoforms a and c, but do not bind strongly to KTI isoforms a and c which have been denatured by moist heat or alkaline treatment or which have been subjected to disulfide exchange; (3) do not bind KTI isoform b; and (4) bind only weakly to KTI when KTI is complexed with trypsin or a similar enzyme. The third specificity pattern is defined by antibodies that (1) recognize KTI, but do not bind BBI; (2) bind equivalently to native KTI isoforms a, b, and c, but do not bind to KTI which has been denatured by moist heat or alkaline treatment or which has been subjected to disulfide exchange; and (3) bind equivalently to uncomplexed KTI and KTI complexed with trypsin or a similar enzyme. Immunoassay methods using the monoclonal antibodies to analyze native KTI specifically in soy-derived foodstuffs and in tissues of soybean plants, to determine isoform content of a sample, and to determine the amount of KTI complexed with trypsin in a sample are described.

3 Claims, 5 Drawing Sheets

OTHER PUBLICATIONS bean Trypsin Inhibitor SBTIA-2," *Cereal Chemistry* 46:136–144 (1969).

L. Rossebo and J. Nordal, "A Serological Method for the Detection fo Trypsin Inhibitor in Commerical Soy Proteins and Its Use in Detecting Soy Protein Addition to Raw Meat Products," *Z. Lebensmitt. Untersuch. Forsch.* 148:69–72 (1972).

R. C. Freed and D. S. Ryan, "Changes in Kunitz Tryps in Inhibitor During Germination of Soybeans: An Immunoelectrophoresis Assay System," *Journal of Food Science* 43: 1316–1319 (1978).

R. C. Freed and D. S. Ryan, "Note on Modification of the Kunitz Soybean Trypsin Inhibitor During Seed Germination," *Cereal Chemistry* 55:534–538 (1978).

A. L. Tan-Wilson, B. R. Rightmire, and K. A. Wilson, "Different Rates of Metabolism of Soybean Proteinase Inhibitors During Germination," *Plant Physiology* 70: 493–497 (1982).

P. M. Hartl, A. L. Tan-Wilson, and K. A. Wilson, "Proteolysis of Kunitz Soybean Trypsin Inhibitor During Gemination," *Phytochemistry* 25:23–26 (1986).

S. E. Dierks, J. E. Butler, and H. B. Richerson, "Altered Recognition of Surface-Adsorbed Compared to Antigen-Bound Antibodies in the ELISA," *Molecular Immunology* 23:403–411 (1986).

E. Offir, M. Trop, and Y. Birk, "Studies of the Antigenicity of Trypsin Inhibitors from Soybeans and Lima Beans," (Abstract), *Israel Journal of Chemistry* 9:17BC–18BC (1971).

G. Kohler and c. Milstein, "Continuous Cultures of Fused Cells Secreting Antibody of Predefined Specificity," *Nature* 256:495–497 (1975).

G. Kohler and C. Milstein, "Derivation of Specific Antibody-producing Tissue Culture and Tumor Lines by Cell Fusion," *European Journal of Immunology* 6:511–519 (1976).

P. Herion, D. Sieberdt, M. Francotte, J. Urbain, and a. Bollen, "Monoclonal Antibodies Against Plasma Protease Inhibitors: II. Production and Characterization of 25 Monoclonal Antibodies Against Human $\alpha_1$-Antitrypsin. Correlation Between Antigenic Structure and Functional Sites," *Bioscience Reports* 4:139–148 (1984).

M. Friedman, O. K. Grosjean, and J. C. Zahnley, "Inactivation of Soya Bean Trypsin Inhibitors by Thiols," *J. Sci. Food Agric.* 33:165–172 (1982).

J. H. Orf and T. Hymowitz, "Genetics of the Kunitz Trypsin Inhibitor: An Antinutritional Factor in Soybeans," *J. of Am. Oil Chemists' Society* 56:722–726 (1978).

M. Friedman and M. R. Gumbmann, "Nutritional Improvement of Soy Flour Through Inactivation of Trypsin Inhibitors by Sodium Sulfite," *Journal of Food Science* 51:1239–1241 (1986).

J. J. Rackis and M. R. Gumbmann, "Protease Inhibitors: Physiological Properties and Nutritional Significance," In: *Antinutrients and Natural Toxicants in Foods*, Ed. R. L. Ory, Food & Nutrition Press, Westport, Connecticut, pp. 203–237 (1981).

Y. Birk, "The Bowman-Birk inhibitors-Trypsin- and Chymotrypsin -Inhibitor from Soybeans," *Int. J. Peptide Protein Res.* 25:113–131 (1985).

Douillard et al., Journal of Immunological Methods, 39 (1980) 309–316, "Enzyme-Linked Immunosorbent Assay for Screening Monoclonal Antibody Production: Use of Intact Cells as Antigen".

MONOCLONAL ANTIBODIES TO SOYBEAN KUNITZ TRYPSIN INHIBITOR AND IMMUNOASSAY METHODS

BACKGROUND OF THE INVENTION

1. Field of the Invention

The invention relates to and has among its objects the provision of hybridomas that produce and secrete monoclonal antibodies which are specific for soybean Kunitz trypsin inhibitor, and to immunoassay methods for the determination of active Kunitz trypsin inhibitor in processed foods and soybean tissue utilizing the monoclonal antibodies.

2. Description of the Art

The protein of soybeans (Glycine max) is widely used in human foods in a variety of forms including infant formulas, tofu, soy protein isolates, soy flour, textured soy fibers, and soy sauce. Soybean protein products, properly processed, serve as an excellent source of low cost, high quality protein for human needs. Soybeans are also widely used as a component of animal feeds and as a major export commodity.

Protease inhibitors constitute at least 6% of the proteins of soybeans. There are two principal types of protease inhibitors found in soybeans, Kunitz trypsin inhibitor (KTI) and the double-headed Bowman-Birk trypsin and chymotrypsin inhibitors (BBI). It has been suggested that protease inhibitors in foods have both deleterious and beneficial effects. Animal studies suggest that active protease inhibitors may be toxic to humans, and may adversely affect nutritional quality; thus, there is an important need to minimize the amount of inhibitors in foods. Recent evidence suggests that some dietary protease inhibitors may have a beneficial anticarcinogenic effect. In addition, protease inhibitors may h=important in plant defenses against insects. Because inhibitors have both beneficial and adverse effects, a need exists to define the nature of inhibitors in foods and determine that is the best balance in the food to have optimum benefit.

Approaches to reduction of native (active) protease inhibitor content are Physical and chemical treatment of soy products and genetic alteration of the soybean crop. Although the protease inhibitor activity is largely inactivated by denaturation through conventionally applied heat treatments of soy flour, 10 to 15% residual activity remains. The problems with this approach are that the nature of the residual activity is difficult to characterize, and the process is costly in energy usage. Reduction of trypsin inhibitor content of soy products through genetic modification of the soybean plant to develop low Kunitz trypsin inhibitor has inherent limitations: desirable nutritional value and potential anticarcinogenic activity may be lost concomitant with the reduction of protease inhibitor content, cross pollination of the genetic variant by a wild-type cultivar could result in reexpression of protease inhibitor gene, and cultivars bred for low Kunitz trypsin inhibitor content would still contain other protease inhibitors. In addition, some protease inhibitors may function to prevent predation of the crops by insects, so that some protease inhibitory activities may be important for the agronomic value of soybean cultivars. With either genetic or physicochemical approaches to the reduction of protease inhibitor activity, the ability to measure low levels of protease inhibitors in soybean tissues and derived food products is essential. Since the effects of plant-derived protease inhibitors are of increasing importance in human and animal nutrition, food safety, and plant genetics, it is important to establish the exact protease inhibitor composition of a sample. What is needed is an assay which has the following characteristics: (1) it can differentiate between the two principal protease inhibitors, KTI and BBI, that is, it is specific for one or the other, (2) it is sufficiently sensitive and accurate to measure the low levels of inhibitors that are present in processed foods, and (3) it can differentiate between native (active) inhibitor and denatured inhibitor in processed samples.

Current assay techniques are not capable of providing this information. With regard to enzyme assays, because both KTI and BBI exist as several isoforms, which are derived from different genes or are produced by proteolysis, it is impossible to establish the exact protease inhibitor composition of a sample through enzymatic assay. Moreover, enzyme assays often give inaccurate results with processed samples having low residual activity as found in commercial foods.

Although immunochemical methods for estimating KTI were reported nearly two decades ago (N. Catsimpoolas and E. Leuthner, *Analytical Biochemistry* 31: 437-447 (1969) and N. Catsimpoolas et al., *Cereal Chemistry* 46: 136-144 (1969)), they have not been adopted by analytical or regulatory laboratories. These methods relied on precipitin analysis, which is insensitive, or binding of complement, an unstable mixture of serum proteins. These methods were applied to the detection of soybean trypsin inhibitor in raw meat products (Rossebo and Nordal, *Z. Lebensmitt. Untersuch. Forsch.* 148: 69-72 (1972)) and to the measurement of KTI in tissues of soybean plants (R. Freed and D. Ryan, *Journal of Food Science* 43: 1316-1319 (1978a) and *Cereal Chemistry* 55: 534-538 (1978b); A. Tan-Wilson et al., *Plant Physiology* 70: 493-497 (1982); and Hartl et al., *Phytochemistry* 25: 23-26 (1986)).

More recently, D. L. Brandon et al. (Abstract, 7th European Immunology Meeting, Jerusalem, Israel, Sept. 8-13, 1985) and D. Brandon and M. Friedman (Abstract, 6th International Congress of Immunology, Toronto, Canada, July 6-11, 1986) reported on polyclonal antibodies prepared by inoculation of rabbits with native KTI and KTI denatured by heat treatment or modified by reaction with agents which induce disulfide exchange. Polyclonal antibodies elicited with denatured KTI were specific only for denatured KTI. In contrast, polyclonal antibodies elicited by native KTI recognized both native and heat-treated KTI indicating that antibodies specific to native KTI could not be produced in rabbits using conventional protcols. Brandon and Friedman, 1986, supra, also reported that preliminary results indicated that monoclonal antibodies to KTI could be produced and that three epitopes (antiboding sites) were identified as present on the molecule. One of these epitopes was retained when pure KTI was denatured. The conditions used were those to prepare a sample for gel electrophoresis -- treatment in solution containing detergent and reducing agent (ca. 1% sodium dodecylsulfate and 0.1% 2-mercaptoethanol) at 100° C. for 2 minutes (Brandon and Friedman, unpublished information). These conditions are known to unfold proteins completely, destroying disulfide bonds and other features of the secondary and tertiary structure of proteins and are unlike the conditions used in food processing (moist heat or alkaline treatment in the absence of detergent and reducing agent).

The production of monoclonal antibodies by fusion of spleen cells and myeloma cells has been described previously by Kohler and Milstein, *Nature* 256: 495–497 (1975) and many other investigators. While monoclonal antibodies against protease inhibitors from animal sources are known (See Herion et al., *Bioscience Reports* 4: 139–148 (1984)), no immunoassays have been described which use monoclonal antibodies to detect specific protease inhibitors in complex samples such as soybeans and processed foods. It was unknown whether sufficiently specific antibodies could be prepared which could differentiate between KTI and BBI, distinguish between native KTI and KTI denatured by heat, and would be useful in detecting low levels of KTI in samples containing multiple protease inhibitors and containing phytate, fat, fiber, and other potentially interfering substances. Further, it was uncertain whether antibodies and assay methods could be developed to identify the particular KTI isoforms present in a sample and to identify whether KTI was bound to trypsin or trypsin-like enzymes. These specificities would be useful in analyzing samples of unknown origin, or for identifying which plant cultivars are represented in a sample. The identification of KTI as part of a complex would allow quantitation under conditions where enzymatic assays would be inaccurate or impossible. Quantitation of complexes would also be important in studying allergic manifestations of soy-containing diets.

While various immunoassays, including enzyme-linked immunosorbent assay (ELISA) methods have been used for quantitation of plasma protease inhibitors, it has not been previously demonstrated that protease inhibitors in general, or KTI specifically, can be labeled with an enzyme in such a way that the antigenic structure is retained. Retention of antigenic structure is essential to achieve the specificity required of the immunoassays. Further, it is known that some proteins undergo structural changes which affect their antigenicity when adsorbed onto plastic assay plates (Dierks at al., *Molecular Immunology* 23: 403–411 (1986)), so it could not be predicted that the antigenic differences among KTI isoforms and their trypsin complexes would be readily measurable utilizing solid-phase assay formats.

SUMMARY OF THE INVENTION

The invention comprises hybrid cell lines (hybridomas) which produce and secrete monoclonal antibodies specific for soybean Kunitz trypsin inhibitor with three distinct patterns of recognition. The first specificity pattern is defined by antibodies which (1) recognize Kunitz trypsin inhibitor, one of the principal protease inhibitors found in soybeans, but do not detect the Bowman-Birk inhibitors,.the other major class of protease inhibitors in soybeans; (2) bind to native KTI isoforms a and b (the isoforms found in soybeans of U.S. origin) but do not react with KTI isoforms a and b which have been denatured by moist heat or alkaline treatment or which have been subjected to disulfide exchange; and (3) do not recognize native KTI isoform c which differs from KTI isoform a in only one amino acid residue.

The second specificity pattern is defined by antibodies that (1) recognize KTI, but do not bind BBI; (2) bind native KTI isoforms a and c, but do not bind strongly to KTI isoforms a and c which have been denatured by moist heat or alkaline treatment or which have been subjected to disulfide exchange; (3) do not bind KTI isoform b; and (4) bind only weakly to KTI when KTI is complexed with trypsin or a similar enzyme.

The third specificity pattern is defined by antibodies that (1) recgonize KTI, but do not bind BBI; (2) bind equivalently to native KTI isoforms a, b, and c, but do not bind to KTI which has been denatured by moist heat or alkaline treatment or which has been subjected to disulfide exchange; and (3) bind equivalently to uncomplexed KTI and KTI complexed with trypsin or a similar enzyme.

Another aspect of the invention is the provision of immunoassay methods for the determination of KTI isoforms a and b which utilize the monoclonal antibodies described above. Because the assays can detect KTI at very low levels, such as are present in processed foods, are specific for KTI but do not detect BBI, and can distinguish between native and denatured KTI, the invention fulfills the important needs described above.

Another important point is that the assay is capable of detecting low levels of KTI in samples containing multiple protease inhibitors and in the presence of phytate, fat, fiber, and other substances which interfere with existing assays.

Another unique aspect of the invention is the provision of immunoassay methods to identify and distinguish any of the three isoforms of KTI present in a sample of soy seeds or a flour or isolate thereof. No other method can accomplish this rapidly and without equivocal results due to the presence of germination forms of KTI which have altered electrophoretic mobility, but retain their antigenicity.

Another aspect of this invention is the provision of a method to determine whether KTI is bound to trypsin or a trypsin-like enzyme in tissues of the soybean plant or in tissues or fluids derived from humans or animals. The ability to detect KTI while it is bound to other proteins is a unique attribute of the methods described herein.

Another aspect of the invention is to provide kits for the assay of native KTI, for determining the isoforms of KTI present in a sample, and for determining whether KTI-trypsin complexes are present in a sample.

In summary, this invention provides a means for (1) distinguishing between the principal protease inhibitors found in soybeans which cannot be distinguished by other methods; (2) accurately and rapidly measuring extremely low levels of native KTI such as are present in processed foods; (3) monitoring active KTI in processes used to inactivate KTI so as to minimize damage to a food and minimize energy requirements of the process, (4) screening soybean seeds in plant breeding studies, (5) screening new plant varieties, plant tissue cultures, and microbes for the expression of the gene coding for KTI, (6) identifying the isoforms of KTI present in samples of soybeans or derived products, and (7) identifying whether or not KTI is present as a complex with trypsin or similar proteases.

In accordance with this discovery, it is an object of the invention to provide monoclonal antibodies specific to KTI which do not crossreact with BBI and methods of using the antibodies for facile and accurate measurement of KTI without crossreaction with BBI.

It is a further object to provide immunoassay methods for measurement of KTI in very low levels in plant tissues and processed foods.

Another object of the invention is to provide monoclonal antibodies which bind to native (active) KTI and do not bind to KTI after denaturation by moist heat or alkaline treatment or subjected to disulfide exchange.

Another object of the invention is to provide monoclonal antibodies and an assay method for determining which isoforms of KTI are present in a sample.

It is a further object to provide monoclonal antibodies and an assay method for determining whether KTI is present as a complex with trypsin or a trypsin-like protease.

It is still a further object to provide a method to study the expression and regulation of plant protease inhibitor genes.

Still another object of the invention is to provide kits useful for the assay of KTI isoforms a, b, and c and their trypsin complexes.

Other objects and advantages of this invention will become readily apparent from the ensuing description.

DETAILED DESCRIPTION OF THE INVENTION

Figure 1:
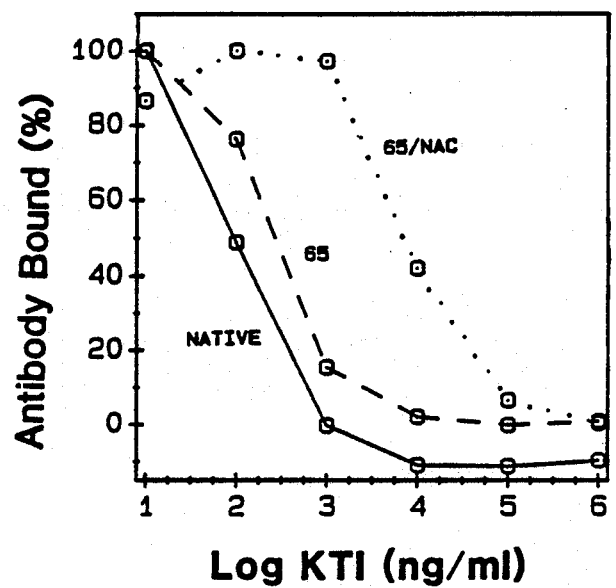
FIG. 1 illustrates competitive ELISA for screening monoclonal antibodies for their ability to discriminate between native and treated KTI.

Statement of Deposit. The following hybridoma cell lines were deposited in the American Type Culture Collection, Rockville. Maryland, with the following accession numbers: ATCC HB 9517 (clone 180); ATCC HB 9516 (clone 129); and ATCC HB 9515 (clone 171).

The invention comprises monoclonal antibodies specific for the native conformation of soybean Kunitz trypsin inhibitor which have three distinct specificity patterns. The antibodies are used to define epitopes present on KTI isoforms and their complexes with trypsin, and to develop assay methods based on the definition of these epitopes. Six epitopes have been found to exist on KTI isoform a in its native configuration.

The immunizing preparation consists of a protein mixture including native KTI. It may contain other soybean proteins, or it may be a homogeneous, pure preparation of a single KTI isoform. The preferred embodiment utilizes a purified preparation of KTI isoform a. This form is commercially available, or can be purified by published protocols.

The preparation of hybridoma cell lines can be done by techniques which are well known to those who are skilled in the art. (See, for example, G. Kohler and C. Milstein, *Nature* 256: 495–497 (1975); *European Journal of Immunology* 6: 511–519 (1976); Koprowski et al., U.S. Pat. No. 4,196,265, and Wands, U.S. Pat. No. 4,271,145, all of which are herein incorporated by reference.)

The choice of animal for immunization is limited by the availability of the fusion partner .the permanent plasmacytoma cell line, and mouse, rat, and human hybridomas have been prePared by many investigators. Mice are preferred because of ease of handling.

Inoculations of the animal can h=by various routes, but the preferred embodiment is an emulsion of protein in complete Freund's adjuvant, via the intraperitoneal route. A series of inoculations, generally at three week intervals, has sufficed, with a good antibody response after two inoculations. Other routes and immunization schedules and other adjuvants or no adjuvant are alternatives. In addition, the sensitization of the cells in vitro is another exbodiment.

The choice of cell line as fusion Partner can influence the results, including frequency of cell fusions and growth characteristics of the resulting hybridoma. However, many cell lines are widely available. In the preferred embodiment, P3-NSl-1-Ag4-1 or the closely related P3X63 -Ag8.653 is used.

Cell fusion can be induced by virus or chemical agent or by an electric field or could occur spontaneously. In the preferred embodiment, poly(ethylene glycol) (PEG), with average molecular weight ca. 1500 is used. A 50% solution by weight in serum-free buffer or medium, approximately 37° C., is convenient to use and reproducibly induces fusion among pelleted spleen and xyeloma cells. The ratio of cells and conditions can vary widely, but a 1:1 mixture appears best. To a pellet containing approximately $10^8$ spleen cells and an equal number of myeloma cells, 0.8 ml of 50% PEG solution is added, with stirring, over a period of 2 minutes. The time period is not critical, and can be varied. The suspension is then diluted gradually with serum-free medium, until 10 ml has been added to the mixture described above. The exact volume and time and temperature can be varied, but 10 ml over 4–5 minutes at 37° C. are convenient conditions which produce consistent results.

Following the cell fusion step, the fused cells can be separated from the myeloma cells by any technique available to the art. The most common and preferred method is to use selective medium in which the myeloma cell will not grow. The preferred cell lines mentioned above lack hypoxanthine phosphoribosyl transferase (HPRT) and will not grow in medium containing aminopterin, since the cells cannot synthesize other purines from the medium constituents. The addition to the medium of $10^{-4}$ M hypoxanthine, $4\times10^{-7}$ M aminopterin, and $1.6\times10^{-5}$ M thymidine, commonly known as HAT medium, is widely used and is the preferred embodiment. The addition of HAT to the culture medium can be made immediately after the fusion, when cells are dispensed into culture vessels, or sometime later, and the cultures are typically maintained in the presence of HAT for about 2 weeks. Following this selection, cultures are transferred to medium lacking aminopterin for a period of time (usually at least 2 "feedings"), and can then be maintained indefinitely in regular medium. A wide variety of media is consistent with the growth of myeloma and hybridoma cell lines, and is generally determined by the requirements of the myeloma cell lines. In a preferred exbodiment, RPMI-1640 basal medium, supplemented with 15% (by volume) horse serum is used. In addition, the following additions are routinely made, although cells are capable of growth in their absence: 1 mM sodium pyruvate, 2 mM glutamine, 10 mM 4-(2-hydroxyethyl)-piperazine-ethanesulfonic acid (HEPES), 50 units/ml penicillin micrograms/ml streptomycin. An antifungal agent can be added if desired or necessary, the preferred embodiment being 100 units/ml nystatin.

The growing colonies are tested for the presence of antibodies that recognize the antigenic determinants of native KTI isoform a. In the preferred embodiment, KTI isoform a is used in screening cell supernatants, but other isoforms or combinations may be used. Detection of hybridoma antibodies can be performed with a variety of assays, but the preferred embodiment is to attach KTI to the surface of assay wells in a multiwell microtitration plate made of polyvinylchloride or polystyrane and widely available commercially. Some lots of polyvinylchloride plates do not bind KTI well, and lots must be tested in advance if this plastic is used. Standard assay methodology and widely used commercial reagents, such as rabbit anti-mouse immunoglobulin G (IgG) antibodies attached to horseradish peroxidase (HRP), can be used to reveal the presence of antibodies in the culture supernatants.

Cloning of hybridomas which are positive for antibody production can be carried out as soon as they are detected. In the preferred embodiment, an accurate count of viable cell density is made prior to the cloning step, after the original cultures have been expanded to at least 1 ml in volume. However, the size of the culture is not critical. Cloning can also be accomplished by limiting dilution in liquid medium or by other means, such as growth of cells in soft agarose, with similar results. In the limiting dilution method, the cell suspension is serially diluted, and the dilution which results in 63% or fewer wells with growth is determined to be the one which yields clones (i.e., on average, 1 cell/well plate, or less). The cloning procedure can be repeated to increase the probability of clonality.

Antibody-secreting hybridomas can be grown in a variety of vessels, including flasks and multiwell dishes. The supernatant medium contains antibody, and can be purified. A commonly used technique to obtain mg to g quantities of antibody is to grow the cell line in the peritoneal cavity of a mouse. The fluid which accumulates in the peritoneal cavity can contain high concentrations of antibody (1 to 10 mg/ml is common). Other means of antibody production, such as growth of hybridomas in hollow fibers, can yield good results also.

The monoclonal antibodies of the invention specific for soybean trypsin inhibitor have three distinct specificity patterns.

Antibodies having the first specificity pattern, exemplified by monoclonal antibody produced and secreted by ATCC HB 9517, (1) recognize KTI, but not BBI; (2) bind to native KTI isoforms a and b but do not bind to KTI isoforms a and b which have been denatured by moist heat or alkaline treatment or which have been subjected to disulfide exchange (i.e., binding reduced at least 100-fold); and (3) do not bind to isoform c (i.e., binding reduced at least 100-fold compared to isoform a).

Antibodies having the second specificity pattern, exemplified by monoclonal antibody produced and secreted by ATCC HB 9516, (1) recognize KTI, but not BBI; (2) bind to native KTI isoforms a and c but do not bind to KTI isoforms a and c which have been denatured by moist heat or alkaline treatment or which have been subjected to disulfide exchange (i.e., binding reduced at least 100-fold); (3) do not bind to isoform b (i.e., binding reduced at least 100-fold compared to isoform a); and (4) bind only weakly to KTI when KTI is complexed with trypsin or a similar enzyme (i.e., binding to KTI-trypsin complex is reduced at least 10-fold over binding to uncomplexed KTI).

Antibodies having the third specificity pattern, exemplified by monoclonal antibody produced and secreted by ATCC HB 9515, (1) recognize KTI, but not BBI; (2) bind equivalently to KTI isoforms a, b, and c, but do not bind to isoforms a, b, and c which have been denatured by moist heat or alkaline treatment or which have been subjected to disulfide exchange (i.e., binding reduced by at least 10-fold); and (3) bind equivalently to uncomplexed KTI and KTI complexed with trypsin or a similar enzyme.

For the purposes of this invention, moist heat is defined as aqueous solutions or suspensions at 75° C. or above for one hour or more; or at relative humidity of 95% or more at 100° C. or more. Alkaline treatment is defined as treatment in aqueous solutions or suspensions at at least 25° C. at pH 12 or above, at 65° C. at pH 11 or above, or at 75° C. at pH 10 or above, with interpolations between these values. Disulfide exchange refers to treatment with any compound which induces breakage and/or rearrangement of the disulfide bonds of native KTI, such as, but not limited to, treatment of aqueous solutions or suspensions with N-acetylcysteine (NAC). The term complexed with trypsin or a similar enzyme includes protease and other inhibitor-binding proteins of animal and plant origin such as chymotrypsin, elastase, plasmin, and the like.

Systematic Screening. To obtain the monoclonal antibodies having the specificity patterns described above, systematic screening is carried out as follows:

Screening for Antibodies which Distinguish Between Native and Denatured KTI. A preliminary screening for antibodies specific for native KTI is performed by a direct binding assay (titration), with selection of antibodies which bind to native KTI, but bind weakly to treated KTI. In a convenient form of the screening, treated KTI is KTI heated in solution at 65° C. (heat-treated KTI) or KTI heated in solution at 65° C. in the presence of NAC (NAC-treated KTI). Antibodies which bind weakly to treated KTI are defined as those wherein binding is reduced at least 20% for heat-treated KTI or at least 50% for NAC-treated KTI. The selected antibodies are next screened by competitive ELISA, with selection of those which bind to treated KTI only in proportion to the trypsin inhibitory activity retaining after treatment. For example, if the treated KTI retains 50% of its original trypsin inhibitory activity, antibodies are selected which have 50% binding to the treated KTI compared to native KTI. In a preferred embodiment, antibodies are selected which have at least 60% reduced binding to heat-treated KTI and at least 95% reduced binding to NAC-treated KTI, as measured by competitive ELISA. This screening is essential for systematically selecting antibodies having the first two specificity patterns.

Systematic Screening of Antibodies for Isoform Specificity. Monoclonal antibodies are screened by direct binding to solid-phase KTI isoforms or by inhibition ELISA with the various isoforms in solution. The inhibition ELISA is performed with either (1) solid-phase KTI (isoform a preferred) and labeled anti-mouse IgG or (2) solid-phase monoclonal antibody, with KTI-horseradish peroxidase (KTI-HRP). The precise conditions can be varied, with the preferred method employing one hour incubations, using HRP as label. In these assays, the binding of an antibody to isoforms b and c is compared to its binding to isoform a. A 100-fold reduction in relative binding activity is the criterion for isoform specificity.

Uses of Monoclonal Antibodies of the Invention.

Measurement of Native KTI. The measurement of native KTI isoforms a and b is carried out using the monoclonal antibodies of the invention. The preferred method is use of ELISA.

ELISA Using labeled Antibody. In this assay, a sample to be analyzed is incubated with monoclonal antibody specific for native KTI. The preferred antibody is one having the first specificity pattern. Portions of this mixture are transferred to wells of any solid phase, such as assay plate, bead or solid-state electronic device, coated with native KTI. After an incubation (one hour is preferred), the solid phase is drained, washed, and rinsed, and bound antibody is detected with an enzyme-labeled anti-mouse IgG reagent (HRP-labeled rabbit antibody is preferred) and suitable substrate, (2,2'-azino-bis-3-ethylbenzthiazolinessulfonic acid (ABTS) is preferred). The assay can be performed using other labels, such as radiolabels or chromophores, or with directly labeled monoclonal anti-KTI.

A standard curve relating the amount of bound monoclonal antibody to KTI concentration is constructed from assays using authentic KTI isoforms a or b. The concentration of KTI in the sample is determined by reference to the standard curve.

ELISA using labeled KTI. In this variation of the assay, monoclonal antibody specific for native KTI is attached to a solid phase, with multiwell plastic microtitration plates the preferred embodiment. The preferred antibody is one having the first specificity pattern. Covalent attachment to a surface, bead, solid-state electronic device or relatively nonspecific adsorption to such surfaces may be employed. Sample to be analyzed is mixed with an appropriate amount of labeled KTI, which can be labeled with an enzyme such as HRP, the preferred method. Other labels, including biotin derivatives or various chromophores, or radiolabels, paramagnetic labels, or even microbes may be used. The mixture of labeled KTI and analyte is applied to the solid phase, and after incubation (one hour preferred), the solid phase is drained, washed, and rinsed, and bound labeled KTI is determined by a method dependent on the surface and label used. In the preferred exbodiment, HRP bound to the plastic dish is determined using ABTS as substrate. The amount of native KTI in the sample is determined with reference to a standard curve as described above.

Determination of Isoform Composition. In this immunoassay, a competitive binding study is performed involving KTI-specific antibodies, KTI isoform a (native or as a labeled species, such as a conjugate with HRP (KTI-HRP)), and KTI isoforms which are present in the test sample. Several assay formats are possible, with either antibodies or KTI as the solid phase. In the preferred embodiment, specific monoclonal antibodies from ATCC HB 9517, ATCC HB 9516, and ATCC HB 9515 are each coated onto a solid phase (plastic assay plates are preferred). The sample is solubilized, if necessary, and mixed with KTI-HRP appropriately diluted, with buffer (bovine serum albumin-phosphate buffered saline-Tween (BSA-PBS-Tween) is preferred). Aliquots of the mixture are applied to solid phase antibody of the third specificity pattern. After an incubation period (one hour is preferred), the solid phase is washed free of unbound material, and bound HRP is assayed (addition of substrate solution containing ABTS is preferred). The results obtained with the sample are compared with a standard curve to determine the amount of KTI present. Next, the assay is Performed with aliquots of the sample diluted to have KTI within the range of 1 to 3 µg/ml. The competitive ELISA is performed on two solid phases, the first coated with antibodies of the first specificity pattern and the second coated with antibodies of the second sPecificity pattern. The ELISA is also performed with a control sample consisting of diluent lacking KTI (e.g., buffer) to determine the maximum amount of labeled KTI bound to each solid phase. The percent of inhibition of binding in the test sample is calculated with reference to the control sample. The isoforms present in the sample are distinguished by the following criteria: if the percent of separated solid phase labeled KTI on the solid phase of the first specificity is at least 90%, then isoform c is present; if the percent of separated solid phase labeled KTI on the solid phase of the first specificity is less than 75%, then isoform a, isoform b, or a mixture of the two is present; if isoform a, isoform b, or a mixture of the two is present and the percent of separated solid phase labeled KTI on the solid phase of the second specificity is less than 20%, then isoform a is present; if isoform a, isoform b, or a mixture is presented the percent of separated solid phase labeled KTI on the solid phase of the second specificity is more than 20%, then isoform b is present. The resulting pattern of competitive inhibition of binding of labeled KTI is described in Table 1. Other formats of the assay are possible, and can be based on the specificity pattern in Table 1 and from the quantitative data in Example 3.

TABLE 1

| | Competitive Inhibition of Binding | | |
|---|---|---|---|
| Isoform | Antibody from ATCC HB 9517 | Antibody from ATCC HB 9516 | Antibody from ATCC HB 9515 |
| a | + | + | + |
| b | + | − | + |
| c | − | + | + |

+ indicates strong inhibition of binding by isoform when indicated antibody binds to solid-phase KTI or when KTI-HRP binds to solid-phase antibody.
− indicates very weak or no inhibition of binding.

Determination of KTI-trypsin Complexes. The analysis of KTI-containing samples to determine whether KTI is present unbound or bound in a complex with trypsin or a similar enzyme is performed using two different monoclonal antibodies specific for KTI. Antibody having the third type of specificity of the invention, exemplified by antibody from ATCC HB 9515, is used to measure all forms of native KTI, whether or not bound to trypsin. Antibody having the second type of specificity of the invention, exemplified by antibody from ATCC HB 9516 is used to measure uncomplexed KTI selectively. The competitive immunoassay techniques described above are convenient and preferred. A standard curve is obtained using as analyte the complex KTI with trypsin. KTI-trypsin complex is calculated as follows:

$$KTI-trypsin = KTI\,TOTAL - KTI\,UNCOMPLEXED$$

This is further described in detail in Example 4 below.

Estimation of BBI. For samples containing isoforms a or b, active KTI is determined as described above. The amount of KTI in the sample is determined following analysis of a dilution series of the sample, with reference to a standard curve obtained using a dilution series of KTI isoform a or KTI isoform b. The midpoint of the titration curve is used to determine the concentration of sample that inhibits binding by 50% ($I_{50}$). The KTI concentration in the sample solution is determined by reading from the standard curve.

Thus, $$I_{50}(KTI, mg/ml)/I_{50}(sample, mg/ml) = mg\ KTI/mg\ sample.$$

The trypsin inhibitor (TI) activity is determined as described in Friedman et al., *Journal of the Science of Food and Agriculture* 33: 165–172 (1982). BBI is estimated as BBI=TI activity in sample (mg/g) - KTI (mg/g) in sample (by ELISA).

Other methods of statistical and graPhical analysis can be used as alternates to this very simple method. The choice of particular technique and reagents depends on the particular application, since simplicity and cost (along other parameters) vary. But anyone skilled in the art could apply the generalized technique.

These procedures for analysis of KTI-containing samples can be readily automated, for example by provision of automatic pipeting equipment and automated ELISA reader and computer. The invention can also be adapted to a variety of kits, in which antibody, suitably labeled KTI, labeled anti-immunoglobulin, substrate, and standards are supplied in separate containers, or, as appropriate, coated on solid phases. The surface could be a plastic assay dish, a bead, or electronic solid-state transducer that would permit on-line monitoring, for example. Reagents may be provided in solid or liquid form. The assay could also be arranged as a qualitative assay--such as might be used in a quality control application. In such a format, the appropriate regents would be coated on surfaces and supplied in solutions at concentrations which would reveal a positive assay if more than a predetermined minimum of KTI were present in the sample.

The sample can consist of any product which may contain KTI, including foods such as soy isolates, soy flour, infant formulas, meat products containing soy extenders, or any tissue derived from a plant or organism expressing a gene product similar to KTI. The sample could be a human or animal tissue, for example in determining the fate of KTI in the digestive tract or its presence on a cell surface, within a cell, or as an immune complex.

EXAMPLES

The following examples are intended only to further illustrate the invention and are not intended to limit the scope of the invention which is described by the claims.

EXAMPLE 1

This example describes determination of KTI using ELISA using labeled KTI.

Trypsin Inhibitors. Kunitz soybean. trypsin inhibitor obtained from Sigma Chemical Co., St. Louis, MO, was characterized by polyacrylamide gel electrophoresis and by inhibition of trypsin as described by M. Friedman et al., 1982, supra. KTI was determined to be isoform a. Standard solutions were prepared in PBS (150 mM NaCl, 5 mM sodium phosphate, pH 7.0) or PBS with 0.01% NaN3 (PBS-N3). The solutions were adjusted to 1 mg/ml based on E280, 1 1mg/ml=1 (B.Kassell, *Methods in Enzymology* 19: 853–862 (1970)) and were stored as aliquots at −20° C.

KTI was treated in a variety of ways to simulate conditions which arise during food processing. Treatment at elevated temperature with or without NAC was carried out as described by Friedman et al. 1982, supra. Briefly described, a sample containing 70 mg of commercial Kunitz trypsin inhibitor and 70 mg of NAC and one containing KTI alone were each dissolved in 10 ml of 0.5 M Tris buffer, pH 8.5. The solutions were heated in a water bath at 25, 45, 65, 75, 85, or 95° C. for 1 hour. The contents were then dialyzed in the cold room for 3 days with frequent changes of deionized water and lyophilized. The trypsin inhibitor content expressed in trypsin inhibitor units (TIU) per milligram (Friedman et al., 1982, supra) was 2.29 for the untreated material, 0.09 for the 65° C. plus NAC-treated sample, and 0.84 for the sample treated at 65° C., and 0.07 for the sample treated at 95° C. Alkaline treatment at pH 8 to 12.5 was conducted as described by Friedman and Liardon, *Journal of Agricultural and Food Chemistry* 33: 666–672 (1985), with samples treated at 25°, 45°, 65°, and 75° C. The measurement of trypsin inhibitor activity and definition of TIU were as described by Friedman et al., 1982, supra.

Purified BBI was obtained from Y. Birk (Faculty of Agriculture, Hebrew University of Jerusalem, Rehovot, Israel).

Antibody Preparation. Mouse antibodies were elicited in Balb/c mice by two intraperitoneal inoculations at 3-week intervals with native KTI emulsified in complete Freund's adjuvant. Antibody production was assessed by EIISA. Monoclonal antibodies were produced as follows. A KTI antibody-producing mouse was inoculated intravenously with 50 $\mu$g of native KTI (isoform a) 3 days prior to cell fusion. Equal numbers of immune spleen cells and xyeloma cells (P3-NS-1-A-g4 or P3X63-Ag8.653, Kearney et al., *Journal of Immunology* 123: 1548–1550 (1979)) were fused by treatment with 50% PEG 1450 (Bethesda Research laboratories, Bethesda, MD), and the fusion suspension was dispersed into 96-well tissue culture plates, 0.2 ml/well, at a cell density of $1.5 \times 10^6$ cells/ml. Hybridomas secreting KTI-specific antibody were identified by ELISA. Fusion culture supernatants were harvested after, two weeks growth, diluted (1:10in PBS or BSA-PBS-Tween, and applied to KTI-coated assay wells. Details are given below. Positive cultures were identified (greater than 0.1 Absorbance units at 415 nm after 15 minutes). Following transfer and expansion of the cultures, hybridomas were cloned by limiting dilution. Clones were expanded in culture, permitting harvest of supernatant, freezing of cell lines, and preparation of ascites fluid. Antibodies are denoted by the number assigned to the cloned hybridomas, e.g., clone 129 produces antibody 129. Monoclonal antibodies were assayed for isotype and light-chain composition by a solid-phase assay similar to the direct-binding assay, but using isotype-and light-chain-specific antibodies conjugated to $\beta$galactosidase (Southern Biotechnology, Birmingham, AL). Myeloma proteins (Litton Bionetics, Kensington, MD) were used to assess the specificity of these antibodies. Clones 127–142 were derived from a fusion with P3-NS-1-Ag4-1 myelomas. Clones 171–180 were derived from a fusion with the P3X63 Ag8.653 cell line.

Screening for Antibodies which Distinguish between Native and Denatured KTI.

Preparation of KTI-coated Assay Plates. KTI isoform a, native or treated as described above, (10 μg/ml, 50 μl/well) was coated on polyvinylchloride or polystyrene assay plates (Costar Co., Cambridge, MA). The plates were incubated for 4 hours and then washed with PBS-Tween and rinsed with distilled water. Remaining sites were blocked by incubating for 1 hour with 100 μl/well of 1% BSA (Miles laboratories, Elkhart, IN) in PBS-Tween solution. Plates were then rewashed and used immediately or stored for up to 1 week in PBS with azide. Assay plates stored longer were less efficient in binding assays.

Direct-binding Assays. Antibody samples to be assayed were serially diluted in PBS or BSA-PBS-Tween. The resulting samples (50 μl/well) were applied to KTI-coated plates, generally in triplicate, and incubated with shaking for 1-2 hours. Plates were emptied, washed, rinsed with distilled water, and drained. Labeled reagent (50 μl/well of HRP-labeled rabbit anti-mouse IgG) diluted in BSA-PBS-Tween was added, and the plates were incubated for 1 hour with shaking, then washed, rinsed and drained. Next, 50 μl of substrate (1 mM ABTS, 6.7 mM $H_2O_2$, 60 mM sodium citrate, pH 7.3) was added, and the absorbance at 415 nm was determined on a plate reader (Model 308, Bio-Tek Instruments, Burlington, VT). Assays were generally read after 15 minutes or terminated by addition of 50 μl/well of 10% sodium dodecylsulfate. These assays demonstrated that most of the monoclonal antibodies had similar binding patterns, with poor discrimination between native and denatured KTI. However antibody from ATCC HB 9517 showed strong preference for native KTI.

Competitive Inhibition Assays. Antibody and native or treated KTI were mixed and preincubated for 1-2 hours at room temperature prior to assay. Antibodies were used at concentrations falling within the linear range, determined by the direct binding assays above. Aliquots of the preincubation mixtures were assayed as described above for the direct binding assays, using assay plates prepared with native KTI. FIG. 1 shows that antibody from AICC HB 9517 is highly specific for native KTI, and discriminates against heat-denatured KTI.

Antibody Purification. Balb/c mice were injected with 2,6,10,14-tetramethylpentadecane (Aldrich Chemical Co., St. Louis, MO) 1 week prior to intraperitoneal inoculation with $10^6$ viable hybridomas. High-titer ascitic fluid and sera were obtained from four of six mice within 3 weeks of inoculation. For use in assays, the IgG fraction was purified from ascitic fluid or spent tissue culture medium by ammonium sulfate precipitation and chromatography on [(diethylamino)-ethyl] cellulose (DE-52, Whatman, Ltd., Maidstone, U.K.).

Enzyme Conjugate. The conjugate of HRP and KTI was synthesized according to P. K. Nakane and A. Kawaoi (Journal of Histology and Cytochemistry 22: 1084–1091 (1974)), using peroxidase from Sigma Chemical Co. (St. louis, MO.) or Scripps Institute (la Jolla, CA).

In brief, the procedure was carried out as follows. 3.8 mg HRP was dialyzed overnight against 0.1 M sodium bicarbonate, pH 8.5, and then 3 h against the same buffer at pH 9.5. The free amino groups of peroxidase were blocked by reaction with trinitrobenzenesulfonic acid, and carbohydrate residues were oxidized by reaction with sodium periodate. After the excess periodate was reacted with ethylene glycol, 3.2 mg KTI was added to the reation mixture. After an incubation of approximately three hours, the resulting aldimine bonds between HRP and KTI were reduced with sodium borohydride. The conjugate was then dialyzed against PBS and purified by gel filtration on Sephadex G-100 (Pharmacia, Uppsala, Sweden) in PBS. The product, analyzed by UV-visible spectroscopy and protein assay (lowry et al., Journal of Biological Chemistry 193: 265–275 (1951)), contained 1.2 moles HR/mole KTI. The stock had a protein concentration of 140 μg/ml, and was used at a final dilution of 1:500 and was stored in the presence of 1% BSA. Peroxidase activity was measured as described above.

ELISA using KTI-HRP. The assay was conducted on assay plates coated with purified IgG anti-KTI (10 μg/ml, 50 μl/ml). Unknowns or standard samples containing KTI were premixed with equal volumes of KTI-HRP and incubated in the assay wells (50 μl/well, 1-2 hours at room temperature with shaking). The binding reaction was complete within one hour, with no change in binding between one and two hours. Plates were again washed and rinsed and bound KTI-HRP assayed.

Figure 2:
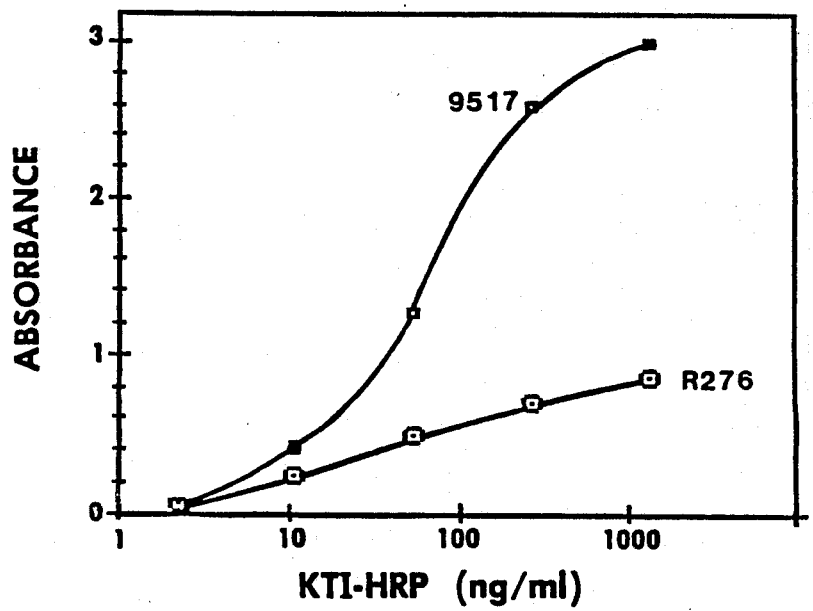
FIG. 2 illustrates the titration of KTI-peroxidase conjugate on two antibody-coated solid phases.

FIG. 2 illustrates the titration of KTI-peroxidase conjugate on two antibody-coated solid phases. Monoclonal antibody from ATCC HB 9517 was prepared as described above. Polyclonal antibody (R276) was elicited from a rabbit by inoculation with KTI emulsified in Freund's adjument, and was used as a solid phase in the titration of KTI peroxidase conjugate for purposes of comparison. Substrate develoPment time was 15 minutes. As is clear from FIG. 2, the monoclonal antibody from ATCC HB 9517 had a five-fold greater binding capacity in the middle range of the titration curve and therefore made a solid phase that was far superior to polyclonal antibody.

Figure 3:
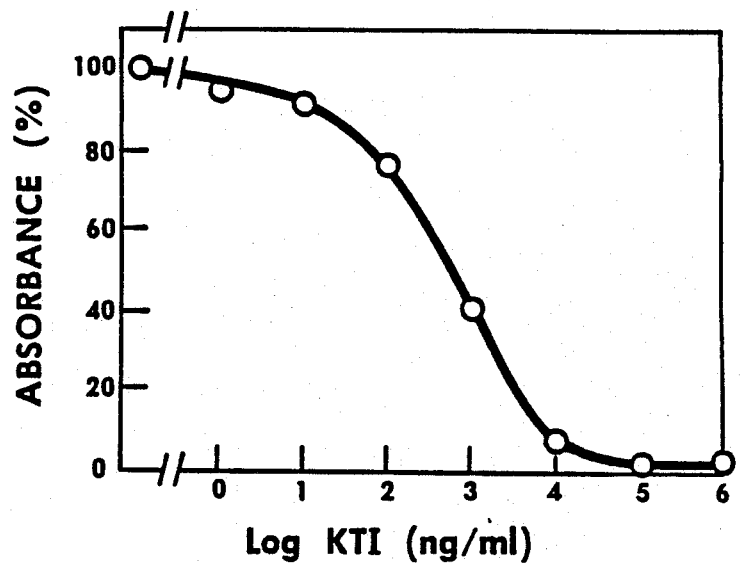
FIG. 3 shows a standard curve for KTI by ELISA using monoclonal antibody from ATCC HB 9517.

A standard curve assay for KTI by (LISA using monoclonal antibody from ATCC HB 9517 is illustrated in FIG. 3. Reaction time was 15 minutes. The working range of the assay is 30 to 3000 ng/ml. The assay was insensitive to BBI, up to a concentration of 1 mg/ml. Between-assay variability for analysis of soy products was 15% expressed as a coefficient of variation.

Analysis of a soybean cultivar lacking the gene for KTI (Ti). Three samples of soybeans from isoline L81-4871, lacking Ti, were obtained from T. Hymowitz (University of Illinois, Urbana, IL). These soybeans were harvested from plants grown in varying degrees of isolation to minimize cross-pollination by cultivars expressing Ti. The KTI content was determined by competitive binding immunoassay using antibody from ATCC HB 9517 and solid-phase KTI. The KTI content of soy meal from two field-grown samples was 0.02 and 0.07 mg KTI/g soybean meal. A greenhouse-grown sample contained 0.0029 mg KTI/g soybean meal. In comparison, the related cultivar expressing the gene for KTI isoform a contained 4.62 mg KTI/g soybean meal. Thus, field-grown samples had approximately 100-fold reduction in KTI by ELISA, and the most isolated, greenhouse-grown sample had greater than 1000-fold reduction in KTI by ELISA.

Figure 4:
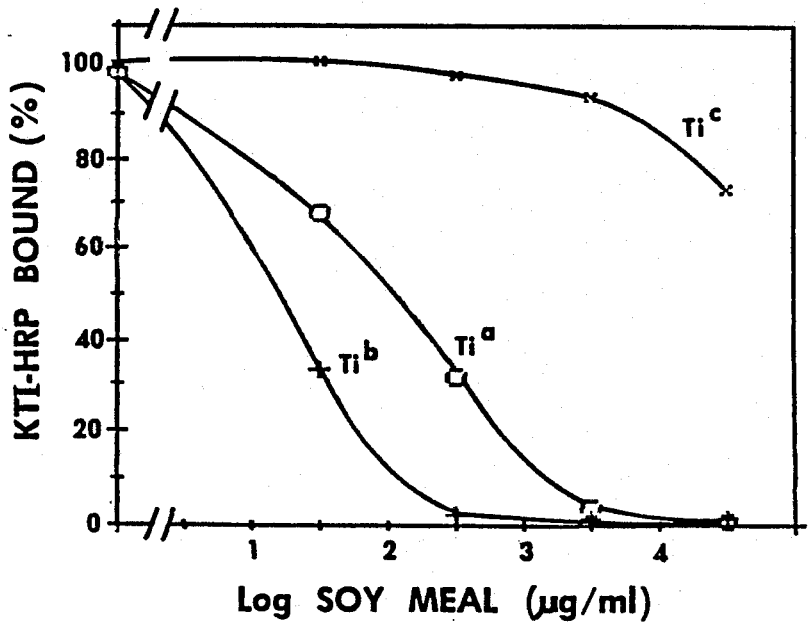
FIG. 4 shows ELISA of soybean meal of seeds of different cultivars expressing the $Ti^a$, $Ti^b$, or $Ti^c$ gene product.

Specificity of ELISA using Antibody from AICC HB 9517 to Isoforms of KTI. Extracts were prepared from soybean meal from seeds of different cultivars expressing the Ti$^a$, Ti$^b$, or Ti$^c$ gene product. The lines and type of KTI are as follows: Williams (Ti$^a$), L82-2024 (Ti$^b$), L82-2051 (Ti$^c$), and L81-4871 (Ti$^-$). Seeds were extracted according to Orf and Hyxowitz (*Journal of American Oil Chemists Society* 56: 722–726 (1979)), and the extracts were stored as frozen aliquots. Extracts were compared by titration in the ELISA using monoclonal antibody from ATCC HB 9517. The results (FIG. 4) indicate that the assay detects both Ti$^a$ and Ti$^b$ and is most sensitive to Ti$^b$. Extracts of seeds expressing Ti$^c$ had only about 1% crossreactivity in this assay.

Figure 5:
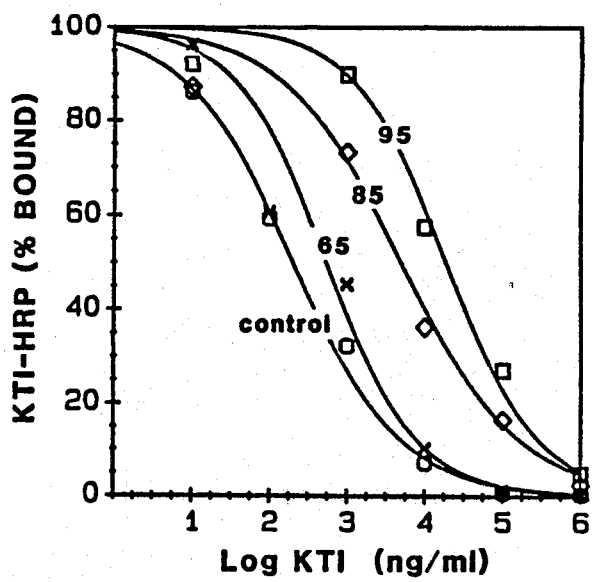
FIG. 5 shows assay curves of KTI heat-treated at 65, 85, and 95° C. and control.
Figure 6:
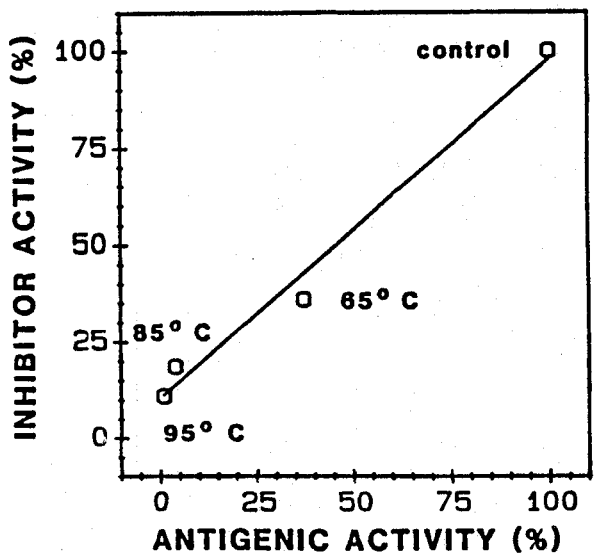
FIG. 6 shows the correlation of antigenicity with the inhibitory activity of KTI.

Analysis of Heat-Treated KTI. Heat-treated KTI prepared as described above at 45, 65, 85, and 95° C. was assayed by ELISA using monoclonal antibody ATCC HB 9517. The analysis of heat-treated KTI is described by a family of curves shown in FIG. 5. The curves are exponential functions calculated by fitting the data to a logistic model. The progressive shifts of the titration curves of heated samples to the right is consistent with decreasing concentration of native KTI. Relative antigenic activity was determined by titration of each sample in the ELISA, and calculation of fitted exponential curves. The concentration of KTI resulting in half maximal (50%) binding of KTI-HRP was determined as a percent relative to the dialyzed control, which produced 50% binding at 201 ng/ml. Thus, the sample treated at 65° produced 50% binding at 545 ng/ml, and was considered to have (201÷545)×100, or 37% antigenic activity. The inhibitory activity of each sample was determined as described by Friedman et al., 1982, supra, and was expressed as a percent of the activity of the dialyzed control (2.31 μg/ml). These values for immunological activities correlated strongly (r=0.99) with the KTI activity detailed enzymatically (FIG. 6).

Analysis of Soy Products.

Soy Flour Extracts. Soy flour samples (Ralston Purina, Co., St. Louis, MO) were used either raw or after heating (75° C.) or after treatment with N (Friedman et al., 1982, supra) or sodium sulfite (Friedman and Gumbmann, *Journal of Food Science* 51: 1239–1241 (1986)). In the NAC treatment, soy flour (200 mg) and NAC (67.4 mg, 0.4 mmol) in 30 ml of 0.5 M Tris buffer were placed in a water-bath at 75° C. for 1 hour. The reaction mixture was then cooled in ice-water. Portions (0.05 ml) of the suspensions were diluted to 0.5 ml with 0.05 M Tris buffer (pH 8.2). Control experiments without NAC were carried out concurrently. In the sodium sulfite treatment, soy flour (700 g) was dispersed in 2.1 liters prewarmed 0.5 M Tris buffer (pH 8.5) and heated with stirring at 75° C. for 1 hour. The contents were then cooled, dialyzed for 3 days against water and lyophilized.

Extracts of the raw or treated soy flour samples were prepared by suspending 100 mg flour in 15 ml 0.5 M Tris Cl buffer, pH 8.5, and stirring for 1 hour at room temperature. The suspension was then clarified by centrifugation (45,000 g-min) and stored as aliquots at −20° C.

Preparation of Food Samples for Immunoassay. Products were obtained from local retail outlets. Infant formulas were canned concentrates. Soyalac (Loma Linda Foods, Riverside, CA), ProSobee (Mead Johnson and Co., Evansville, IN), and Isomil (Ross Laboratories, Columbus, OH). Samples were divided into aliquots (200 μl), and then a small volume of internal standard (KTI, 1 mg/ml in PBS) or diluent was added. Serial dilutions were then made in PBS containing 0.05% Tween-20 (Sigma Chemical Co.) and 10 mg/ml bovine serum albumin (PBS-Tween+BSA). In addition to the soy-based formulas, a milk-based formula (Similac, Ross Laboratories, Columbus, OH) was analyzed as a control.

Tofu (Azumaya, Inc., San Francisco, CA) was sliced, rinsed with distilled water and PBS, and drained on absorbent Paper. The sample was weighed, and then triturated with 0.5 M Tris-Cl buffer, pH 8.5 (10 ml per g tofu). The suspension was stirred for 1 hour at room temperature, and then centrifuged (45,000 g-min). The supernatant was refrigerated and assayed within 24 hours. Soy sauce (Kikkoman, Walorth, WI) had a pH of 4.8, and was neutralized with 10 N NaOH. It was analyzed exactly as described for the infant formulas.

Figure 7:
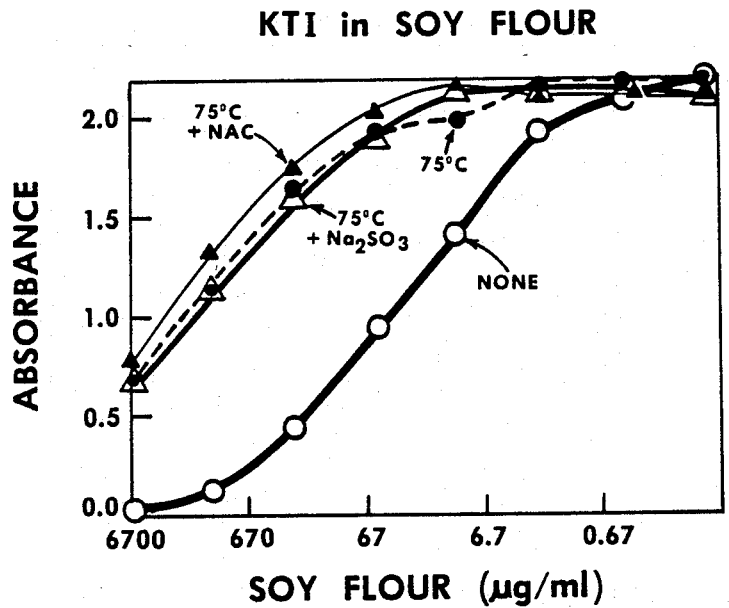
FIG. 7 shows the ELISA analysis of raw and processed soy flours.

ELISA Analysis. The EIISA analysis of raw and processed soy flours using monoclonal antibody from ATCC HB 9517 is illustrated in FIG. 7. The ELISA results indicate active KTI concentration (mg/g flour) as follows: raw flour, 7.5; sodium sulfite-treated flour, 0.15; heat-treated (75° C.), 0.15; treated with NAC (75° C.), 0.094. Based on enzymatic assay, the activity of the flours (TIU/g) was as follows: raw flour, 71; sodium sulfite-treated flour, 1.6; heat-treated (75° C.), 12.5; treated with NAC (75° C.), 1.5.

Figure 8:
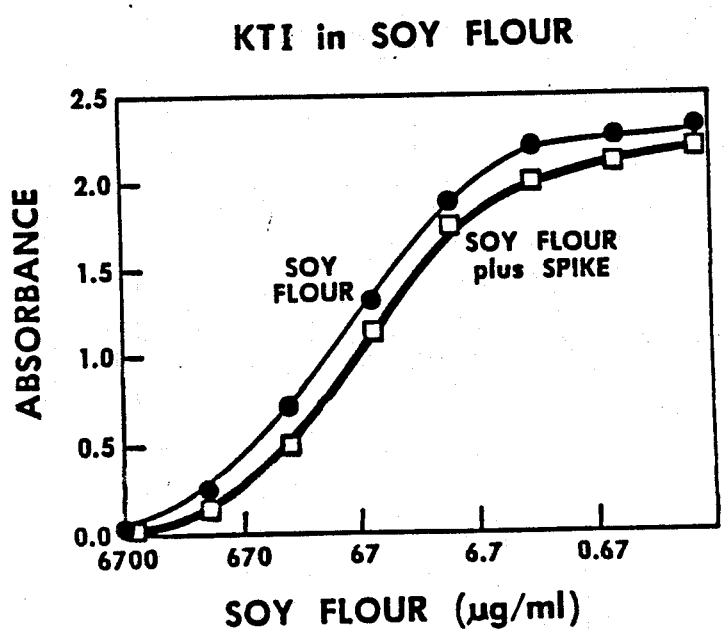
FIG. 8 illustrates an ELISA analysis using a "spike" of purified KTI as an internal standard.

The KTI content was also estimated by the shift in the ELISA assay curve caused by the addition of a "spike" of native KTI, as an internal standard. An extract of raw soy flour was analyzed with and without the addition of purified KTI (29.1 μg/ml). The spike increased the KTI content of the sample by 75% resulting in an estimate of KTI as 6 mg/g soy flour (FIG. 8). It is clear that the processed flours with low activity (82 to 98% reduction of TI activity) also had low immunologic activity (98 to 99% loss in activity in ELISA). The contribution of other inhibitors to the trypsin inhibitory activity can be estimated by combining the results of enzymatic and ELISA analyses. Using the value of 2.9 TIU/mg for purified KTI (Friedman et al., 1982, supra) and the results of ELISA analysis, the KTI content of soy flours can h=computed as a percentage of total TI activity measured enzymatically (Table 2). Most of the remaining TI activity is presumed to be BBI, with some possible due to nonspecific inhibitors such as phytate. The analysis of other commercial soy-based food products by ELISA is summarized in Table 3. In Table 3, the KTI concentration is expressed as μg/ml for liquid samples, μg/g for flour and tofu. All results are based on two independent assays, with the average deviation from the mean indicated, except for Isomil, which was assayed once, with the estimated within-assay error shown. Protein content stated on the label of the formula was used in calculations. Values for other soy products were based on Pennington and Church, *Bowes & Church's Food Values of Portions Commonly Used*, 14th ed., J. B. Lippincott, Philadelphia, pp. 126, 158 (1984). Serving size was 200 ml of reconstituted formula, 112 g of tofu, 18 g of soy sauce, and 10 g for flour.

TABLE 2

| Treatment | Total Trypsin Inhibitor Content by Enzyme Assay (TIU/g) | KTI Content by ELISA | | |
|---|---|---|---|---|
| | | (mg/g) | (TIU/g) | % of Total TIU |
| None | 71 | 7.5 | 22 | 31 |
| Heat (75° C.) | 13 | 0.15 | 0.44 | 3.5 |
| Sodium sulfite (75° C.) | 1.6 | 0.15 | 0.44 | 27 |

TABLE 2-continued

| Treatment | Total Trypsin Inhibitor Content by Enzyme Assay (TIU/g) | KTI Content by ELISA | | |
|---|---|---|---|---|
| | | (mg/g) | (TIU/g) | % of Total TIU |
| N-acetyl cysteine (75° C.) | 1.5 | 0.094 | 0.27 | 18 |

TABLE 3

| Product | Concentration | mg/g protein | mg/serving |
|---|---|---|---|
| Infant formulas (concentrates) | | | |
| Prosobee | 12.7 ± 0.9 | 0.31 | 1.2 |
| Soyalac | 5.0 ± 0.5 | 0.12 | 0.5 |
| Isomil | 7.5 ± 0.9 | 0.21 | 0.75 |
| Similac (control) | <0.1 | <0.003 | <0.01 |
| Tofu | 4.8 ± 1.6 | 0.06 | 0.54 |
| Soy sauce | 1.3 ± 0.2 | 0.013 | 0.02 |
| Soy flour (raw) | 7750 ± 260 | 19 | 78 |

EXAMPLE 2

Figure 9:
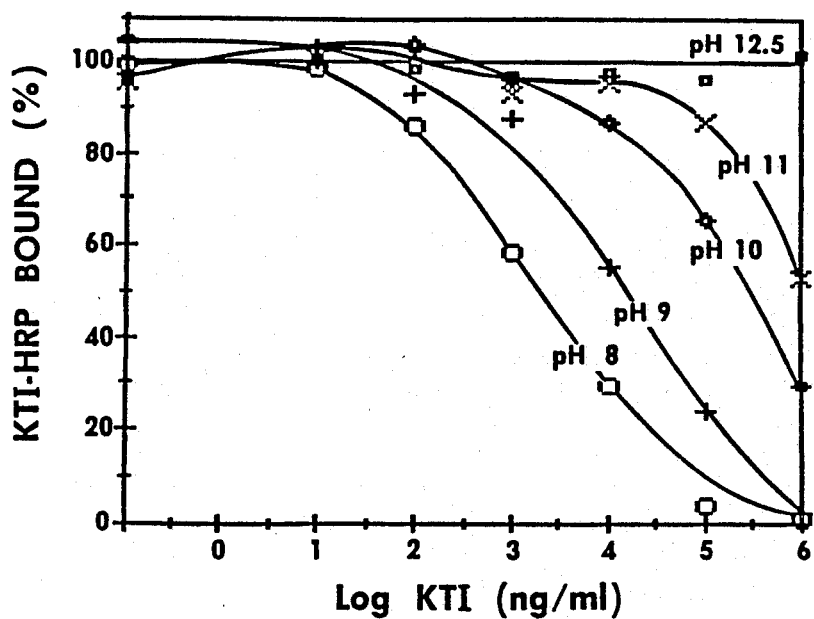
FIG. 9 shows the effect of pH on KTI antigenicity at 65° C.

This example describes the effect of alkaline treatment on KTI. Since soy protein is often processed commercially under alkaline conditions, the influence of alkalinity on antigenic activity of KTI was studied. Alkali treatment was carried as follows: KTI (Sigma Chemical, Co., St. louis, MO) was suspended in solvent (0.05 M borate buffer of appropriate pH). (Each flask was stoppered, and the flasks were placed into a water bath at the appropriate temperature. At the end of the treatment, the flasks were cooled and the final pH measured with a Beckman 84 research pH meter. The contents in Spectra/Por 4 dialysis tubing, molecular cutoff 12000 (Spectrum Medical Industries, Los Angeles, CA), were then immediately dialyzed against 0.25% acetic acid for one day, and thereafter against distilled water for two days. The samples were then lyophilized. Samples were then titrated in the ELISA using monoclonal antibody from AICC HB 9517 as described in Example 1 above. Titration curves for samples treated at 65° C. at various pHs are illustrated in FIG. 9. The activities of the samples (mg KTI/g) were as follows: pH 8, 536; pH 9, 260; pH 10, 243; pH 11, 200; and pH 12.5, 13. It is apparent that at 65° C. alkalinity causes antigenic and functional changes in KTI and these can h=measured in the ELISA using the novel monoclonal antibodies of the invention.

EXAMPLE 3

This example illustrates the identification of KTI isoforms. The interaction of purified, native KTI isoforms with monclonal antibodies from ATCC HB 9515, ATCC HB 9516, and ATCC HB 9517 was examined. Each of the three antibodies of the invention was used to prepare a solid phase, and the binding of each isoform was determined by ELISA using labeled KTI, as described in Example 1. The concentration of KTI isoform producing 50% inhibition of binding was calculated from each assay curve. The values, summarized in Table 4, are relative $I_{50}$ concentration expressed as μg/ml, with the value for isoform a considered 1 for each antibody. The actual $I_{50}$ values for isoform a are 1.6 (antibody from AICC HB 9517), 0.34 (antibody from AICC HB 9516), and 0.43 (antibody from ATCC HB 9515). There are three patterns of binding inhibition, as follows: (a) equivalent inhibition by the three isoforms (antibody from ATCC HB 9515); (b) preferential inhibition by isoforms a and c (antibody from AICC HB 9516); (c) preferential inhibition by isoforms a and b (antibody from ATCC HB 9517). Thus, any one isoform produces a unique inhibition Pattern. (This pattern is summarized in Table 1, above.)

TABLE 4

| | Antibody from ATCC HB 9517 | Antibody from ATCC HB 9516 | Antibody from ATCC HB 9515 |
|---|---|---|---|
| Isoform a | 1 | 1 | 1 |
| Isoform b | 0.13 | 180 | 0.79 |
| Isoform c | 450 | 1.7 | 0.87 |

EXAMPLE 4

Figure 10:
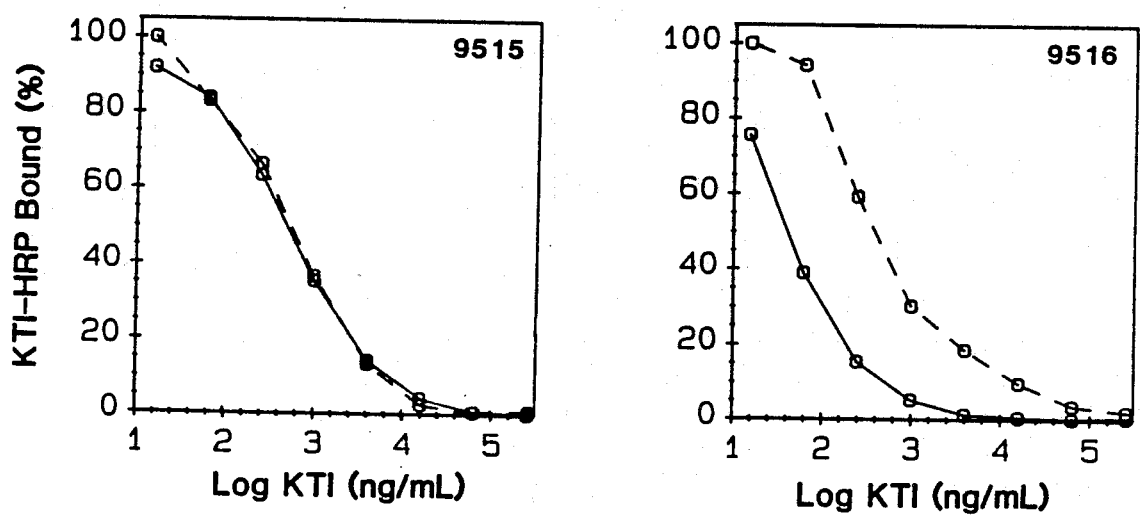
FIG. 10 shows competitive binding analysis of KTI and KTI-trypsin.

This example describes the analysis of KTI-trypsin complexes. Two solid phases were prepared, using antibodies from ATCC HB 9516 and ATCC HB 9515. The competitive binding of KTI and KTI-trypsin with KTI-HRP was analyzed, as shown in FIG. 10. Antibody from ATCC HB 9515 binds KTI and KTI-trypsin equivalently, as shown by identical inhibition curves. Antibody from ATCC HB 9516 binds the KTI-trypsin complex poorly compared to its binding of KTI, as indicated by a ten-fold shift in the $I_{50}$. Thus, the difference in the KTI content of a sample as measured with the two antibodies, permits an estimate of the amount of KTI present as a complex with trypsin or a similar enzyme.

It is understood that the foregoing detailed description is given merely by way of illustration and that modification and variations may be made therein without departing from the spirit and scope of the invention.

Having thus described our invention, we claim:

1. A continuous hybrid cell line which produces and secretes monoclonal antibody specific for soybean Kunitz trypsin inhibitor (KTI) which:
    (a) re acts and binds with KTI isoforms a and b;
    (b) does not react with Bowman-Birk inhibitors;
    (c) does not react with KTI isoforms a and b which have been denatured by moist heat or alkaline treatment or which have been subjected to disulfide exchange; and
    (d) does not react with KTI isoform c;
wherein said cell line is ATCC HB 9517.

2. Monoclonal antibody produced and secreted by the continuous cell line of claim 1.

3. A method for determining KTI isoform composition of a sample, which comprises:
    (a) mixing a first subsample of a sample with labeled KTI to form a mixture;
    (b) contacting said mixture with a solid phase coated with monoclonal antibody which binds equivalently to KTI isoforms a, b, and c to obtain solid phase labeled KTI and unbound labeled KTI;
    (c) separating said solid phase labeled KTI from said unbound labeled KTI;
    (d) measuring the amount of separated solid phase labeled KTI;
    (e) determining the amount of KTI in said first subsample by comparing the amount of measured separated solid phase labeled KTI to a standard curve;
    (f) diluting a second subsample of said sample so that the amount of KTI in said second subsample is within a range of 1 to 3 μg/ml;
    (g) mixing said diluted second subsample with labeled KTI to form a mixture;

(h) taking a first aliquot of said mixture of step (g) and contact said aliquot with a solid phase coated with monoclonal antibody which reacts and binds with KTI isoforms a and b, but does not react with KTI isoform c wherein said monoclonal antibody is produced and secreted by a continuous hybrid cell line designated ATCC HB 9517 to obtain solid phase labeled KTI and unbound labeled KTI;

(i) taking a second aliquot of said mixture of step (g) and contacting it with a solid phase coated with monoclonal antibody which reacts and binds with KTI isoforms a and c but does not react with KTI isoform b to obtain solid phase labeled KTI and unbound labeled KTI;

(j) separating said solid phase labeled KTI from said unbound labeled KTI in said first and second aliquots;

(k) measuring the amount of separated solid phase labeled KTI in said first and second aliquots;

(l) preparing a positive control by using a diluent lacking KTI as a control sample and carrying out steps (i)-(k)

(m) calculating the percent of separated solid phase labeled KTI bound to each solid phase by comparison to said positive control;

(n) distinguishing the isoforms of KTI present in said sample by the following criteria;
  (i) if the percent of separated solid phase labeled KTI on said solid phase coated with monoclonal antibody which reacts and binds with KTI isoforms a and b but does not react with KTI isoform c is at least 90%, then isoform c is present;
  (ii) if the percent of separated solid phase labeled KTI on said solid phase coated with monoclonal antibody which reacts and binds with KTI isoforms a and b but does not react with KTI isoform c is less than 75%, then, isoform a, isoform b, or a mixture of a and b is present;
  (iii) if isoform a, isoform b, or a mixture of a and b is present and the percent of separated solid phase labeled KTI on the solid phase coated with monoclonal antibody which reacts and binds with KTI isoforms a and c but does not react with KTI isoform b is less than 20%, then isoform a is present; and
  (iv) if isoform a, isoform b, or a mixture of a and b is present and the percent of separated solid phase labeled KTI on the solid phase coated with monoclonal antibody which reacts and binds with KTI isoforms a and c but does not react with KTI isoform b is more than 20%, then isoform b is present.

* * * * *